United States Patent [19]
Hubner, Jr.

[11] Patent Number: 4,941,503
[45] Date of Patent: Jul. 17, 1990

[54] VACUUM ASSEMBLY INCLUDING AN IMPROVED VACUUM RELIEF VALVE ASSEMBLY

[75] Inventor: Henry H. Hubner, Jr., Amityville, N.Y.

[73] Assignee: Air Techniques Incorporated, Hicksville, N.Y.

[21] Appl. No.: 193,769

[22] Filed: May 13, 1988

[51] Int. Cl.$^5$ .............................................. F16K 17/04
[52] U.S. Cl. .................. 137/454.2; 137/514; 137/526; 137/541
[58] Field of Search .............. 137/454.2, 514, 526, 137/541

[56] References Cited

U.S. PATENT DOCUMENTS

| | | | |
|---|---|---|---|
| 1,327,494 | 1/1920 | Sims | 137/526 |
| 2,308,583 | 1/1943 | Berges | 137/526 |
| 4,305,425 | 12/1981 | Mackal | 137/541 |
| 4,750,516 | 6/1988 | Heffner | 137/514 |

*Primary Examiner*—Robert G. Nilson
*Attorney, Agent, or Firm*—Louis E. Marn

[57] ABSTRACT

There is disclosed a vacuum assembly including a manifold housing having one port in fluid communication via a conduit with the suction side of a pump and wherein a user site is in fluid flow via a conduit with another port or the manifold housing and wherein a vacuum relief valve assembly is positioned within the manifold housing and includes a valve disc of a spring loaded valve disc assembly in line contact with a bevelled valve seat of a valve body of the vacuum relief valve assembly thereby defining a valve seat of line contact wherein the area downstream of the valve seat is greater than the area at the valve seat.

8 Claims, 1 Drawing Sheet

VACUUM ASSEMBLY INCLUDING AN IMPROVED VACUUM RELIEF VALVE ASSEMBLY

FIELD OF THE INVENTION

This invention relates to vacuum assemblies, and more particularly to a vacuum assembly for maintaining a substantially constant vacuum (pressure) level for a highly variable fluid flow volume.

BACKGROUND OF THE INVENTION

In the dental field, vacuum assemblies including related conduit and tubing are used to remove saliva together with particulate material or debris in the oral cavity of one undergoing various dental procedures. Many devices have been manufactured for insertion into the oral cavity to provide the means for saliva withdrawal under vacuum, which minimizes complete stoppage of flow in the conduit or tubing to the source of a suction side of a pump, since stoppage may result in tissue being drawn into the orifice or orifices of such devices and to thereby arrest fluid flow to the extent that damage results to the tissue drawn into such orifice and orifices.

Various devices and in particular, vacuum relief valves, such as spring loaded ball valves, guided poppet valves and the like have been utilized in vacuum assemblies to obviate the problem of fluid flow stoppage and tissue damage. However, any such vacuum valve assemblies overreact with concomitant fluid flow irregularities and vacuum (pressure) oscillations in the vacuum line resulting in possible tissue damage and failure to maintain optimum levels of vacuum, i.e. generally about 10±2 inches of mercury.

OBJECT OF THE PRESENT INVENTION

An object of the present invention is to provide a vacuum assembly including an improved vacuum relief valve assembly which timely reacts to a reduction or stoppage of flow while maintaining predetermined pressure levels of vacuum.

Another object of the present invention is to provide a vacuum assembly including an improved vacuum relief valve assembly which maintains fluid flow at predetermined levels without overreacting to an interruption in fluid flow to user equipment.

Still another object of the present invention is to provide a vacuum assembly including an improved vacuum relief valve assembly which minimizes mechanical interruption to fluid flow in a vacuum line.

SUMMARY OF THE INVENTION

These and other objects of the present invention are achieved in a vacuum assembly including a manifold housing having one port in fluid communication via a conduit with the suction side of a pump and wherein a user site is in fluid flow via a conduit with another port of the manifold housing and wherein a vacuum relief valve assembly is positioned within the manifold housing and includes a valve disc of a spring loaded valve disc assembly in annular line or narrow area contact with a bevelled valve seat of a valve body of the vacuum relief valve assembly thereby defining a valve seat of annular line or narrow area contact.

BRIEF DESCRIPTION OF THE DRAWING

Further objects and advantages of the present invention will become apparent upon consideration of the detailed disclosure thereof, especially when taken with the accompanying drawing which is a cross-sectional view of the vacuum relief valve assembly in a schematic flow diagram of the vacuum assembly.

DETAILED DESCRIPTION OF THE INVENTION

Figure 1:
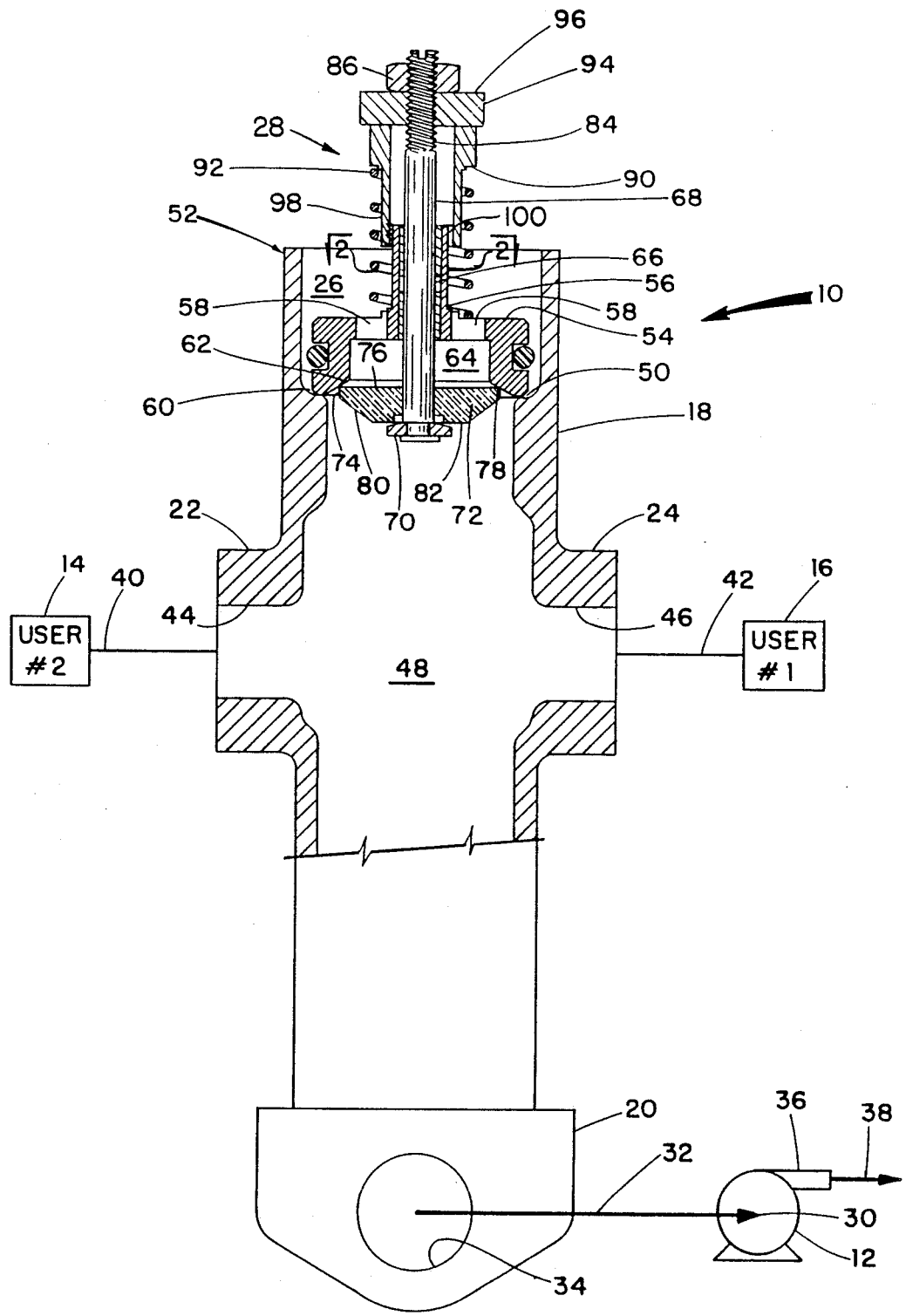

Referring now to the drawing, there is illustrated a schematic flow diagram of the vacuum assembly of the present invention, generally indicated as 10, and comprised of a vacuum pump 12, user stations 14 and 16, a manifold housing 18 including outlet port 20, inlet ports 22 and 24, and an upper chamber 26, and a vacuum relief valve assembly, generally indicated as 28 positioned within the upper chamber 26 of the manifold housing 18. A suction side 30 of the vacuum pump 12 is connected by a conduit 32 to an orifice 34 formed in the port 20 of the manifold housing 18. The discharge side 36 of the vacuum pump is in fluid communication via conduit 38 with the atmosphere. User stations 14 and 16 are connected via conduits 40 and 42 to an orifice 44 and 46 formed in inlet ports 22 and 24, respectively of the manifold housing 18. The manifold housing 18 is formed with a plenum chamber 48 in fluid communication with the conduits 32, 40 and 42 and with the upper chamber 26 defined by an inwardly extending shoulder portion 50 and an upper end 52 of the manifold housing 18.

The vacuum relief valve assembly 28 is positioned within the upper chamber 26 of the manifold housing 18 and is comprised of a valve body 54 having an upwardly extending annular cylinder 56 and axially-formed radial orifices 58 with a lower surface portion 60 of the valve body 54 of the vacuum relief valve assembly 28 contacting the shoulder portion 50 of the manifold housing 18. Formed inwardly of the lower surface portion 60 of the valve body 54 is an upwardly and inwardly extending bevelled or frusto-conically shaped surface 62 terminating in a centrally-formed chamber 64 in fluid communication to the atmosphere via the axially-formed radial orifices 58 and the chamber 26.

The annular cylinder 56 of the valve body 54 is formed with a channel 66 in coaxial alignment with the axis of the vacuum relief valve assembly 28. Disposed within the channel 66 is a shaft 68 having a retaining member 70 affixed to a lower end portion thereof for retaining a generally inverted frusto-conically-shaped valve disc member 72 formed of a plastic material, such as nylon. The valve disc member 72 includes a circumferentially-extending surface portion 74 defining with a top surface 76 a circumferential line or narrow area contact surface 78 for engaging the bevelled or frusto-conically shaped surface 62 of the valve body 54. To provide for adequate fluid flow with minimal, if any chattering, an area defined by the surface portion 74 of the valve disc member 72 with the surface 62 of the valve body 54 is greater than any area defined by the surface 62 of the valve body 54 with the contact surface 78 of valve disc member 72. From a lower portion of the surface portion 74 of the valve disc member 72, there is formed a downwardly and inwardly extending frusto-conically shaped surface 80 terminating at a lower surface portion 82 for engaging the retaining member 70 and in parallelled relationship to the upper surface portion 76 thereof.

The upper portion of the shaft 68 is formed with a threaded portion 84 for receiving a threaded locking nut 86. Positioned about the annular cylinder 56 of the valve body 54 is a cylindrically-shaped dampening member 88 including an intermediate shoulder portion 90 for retaining with a preselect tensioning level, a coil spring 92 with the valve body 54. The dampening member 88 is retained about the annular cylinder 56 by an adjusting nut 94 including a knurled outer surface 96 and maintained in a preselect position by the thread locking nut 86 to achieve any such preselect tensioning level, as more fully hereinafter discussed. The dampening member 88 is formed with slots 98 defined by legs 100 to allow slidable movement with dampening by friction about the annular cylinder 56 of the valve body member 54 and to permit adjustment to the spring tension of the coil spring 92.

The frictional dampening in this embodiment, for example (which is equivalent to many other dampening techniques for example but not limited to dash pots and devices similar to shock adsorbers), is obtained due to the radially-formed outwardly-extending legs 100 forming the slots 98, of dampening member 88 which in turn produces a normal and concomitant dampening friction force between the annular cylinder 56 to the dampening member 88 so as to oppose excessive undampened motion of the subassembly comprised of the valve disc member 72 and the parts interconnecting the valve disc member 72 to the dampening member 88.

In operation, assuming no vacuum requirements for the user stations 14 and 16, upon energizing the vacuum pump 12, a vacuum of from 8 to 12 inches of mercury, preferably 10 inches of mercury is placed on the line 32, and thus in the plenum chamber 48. Absent any fluid flow relationship with user station 14 or 16, the vacuum in the plenum chamber 48 slowly approaches the maximum capabilities, namely about 22 inches of mercury of the vacuum pump 12 and could result in damage to the vacuum pump 12, however the vacuum relief valve assembly 28 disposed in the chamber 26 of the manifold housing 18 permits auto-adjustment to a preselect equilibrium level of vacuum. Any desired level of vacuum is attained as a function of the spring tension of the spring 92 to maintain the shaft member 66 in an uppermost position to maintain the circumferential line or point contact 78 between valve disc member 72 and the bevelled surface 60 of the valve housing 54. At any predetermined desired level of vacuum, the compressive force in the coil spring 92 is less then the force generated by the vacuum and causes the shaft member 68 to be proportionately displaced downwardly to provide for fluid flow or venting of the plenum chamber 48 between the valve disc member 72 and the valve housing 54 and thus with the chamber 64 and orifices 58 in the absence of any user requirement. The valve disc member 72 will remain in an opened position to provide for the predetermined level of vacuum.

Upon demand, either or both of user stations 14 and 16 are provided with a source of vacuum via conduits 40 and 42, respectively, for continuous or intermittent operation. An increase in user requirements causes the disc member 72 to rise and thereby decreases the flow area between bevelled surface 62 of the valve body 54 and bevelled surface 78 of the valve disc member 72 until there is contact of such bevelled surfaces to arrest the venting of fluid flow relationship between the plenum chamber 48 of the manifold housing 18 as hereinabove described.

Should either user station discontinue vacuum usage or should an interruption occur as a result of tissue intake into an orifice of an oral suction removal device, immediate response to prevent undue reduction of the level of vacuum to deleterious low pressures is provided by the operation of the vacuum relief valve assembly 28, and in particular by the lowering of the valve disc member 72 with respect to the valve housing 54 to provide a uniform vacuum pressure level without deviation of level of less than 8 to 12 inches of mercury. The reason for a uniform range of vacuum pressure results from fluid flow through or between the valve housing 54 and the valve disc member 72 wherein there is an increase in area defined by the space between the surface portion 79 of valve disc member 72 and the surface 62 of the valve housing 54 at any open position of valve disc member 72 with respect to the valve housing 54.

In accordance with the present invention, there is achieved a desired response and stable equilibrium of uniform pressure (vacuum) in spite of unstable and interrupted fluid flow in the system including the following principles:

(1) A precise and accurately adjusted and preloaded spring which is compressed and maintains the disc seated against the valve seat to allow maximum fluid flow for the user's at little or no degradation of the vacuum pressure, up to a maximum design fluid flow rate for the system;

(2) A large area valve disc which: (a) allows a small pressure difference across the disc to open the valve thereby maintaining a very uniform pressure in the system when the fluid flow rate of the user is suddenly diminished due to reduction of the number of users or due to blockage in part of the system, and (b) provides a large flow area through the valve even for small valve disc displacements so that large variations in fluid flow rates can be accommodated for small changes in pressure from the design vacuum (pressure) condition; and (3) A dampening mechanism (by friction or other method) which reduces, stabilizes and equilibrates the vibrations of the spring-mass system (defined by the preloaded spring and the valve disc/stem assembly) to prevent uncontrolled oscillations which would otherwise exacerbate the undesirable aspects of pressure fluctuations and non-uniform fluid flow for the user and for the vacuum pump.

While the invention herein has been described in connection with an exemplary embodiment thereof, it will be understood that many modifications will be apparent to those of ordinary skill in the art and that this application is intended to cover any adaptations or variations thereof. Therefore, it is manifestly intended that this invention be only limited by the claims and the equivalents thereof.

What is claimed is:

1. A vacuum assembly for maintaining a uniform pressure level of vacuum under conditions of non-uniform fluid flow in a system which comprises:
 a manifold housing defining a manifold chamber and having an outlet port, one or more inlet ports and a valve receiving chamber in fluid communication with said manifold chamber,
 a vacuum source means in fluid communication with said outlet port of said manifold housing to place said manifold chamber under vacuum, a user station in fluid communication via said inlet port with said manifold chamber of said manifold housing; and a vacuum relief valve assembly disposed in said valve receiving chamber of said manifold housing and enclosing said manifold chamber and comprised of a valve body in which is slidably positioned a valve stem including a valve disc, said valve body defining a chamber and formed with a seating surface, dampening means for stabilizing vibration between said valve stem and said valve body, said valve disc being spring loaded and contacting said seating surface in line contact relationship, a variable area between said valve disc with said seating surface in an opened position being greater than an area defined at inception of fluid flow between said valve disc and said seating surface.

2. The vacuum assembly as defined in claim 1 wherein said manifold housing has a plurality of inlet ports.

3. The vacuum assembly as defined in claim 1 wherein said valve body is biased to a closed position at from 8 to 12 inches of mercury in said manifold chamber.

4. The vacuum assembly as defined in claim 3 wherein said valve body is biased to a closed position at 10 inches of mercury.

5. The vacuum assembly as defined in claim 1 wherein said dampening means is a dampening member disposed on said valve stem for frictionally engaging an annular cylinder of said valve body.

6. The vacuum assembly as defined in claim 5 wherein said dampening member is formed with a plurality of legs defining slots for frictionally engaging said annular cylinder.

7. The vacuum assembly as defined in claim 1 wherein an area between said manifold chamber and said valve seat is greater than an area defined between said line contact of seating surface of said valve body and said valve disc at any position thereof.

8. The vacuum assembly as defined in claim 1 wherein said valve seat is formed with a surface portion extending from said line contact relationship to define with said seating surface of said valve body an area greater than an area defined by said seating surface of said valve body and said valve seat at any position thereof.

* * * * *

UNITED STATES PATENT AND TRADEMARK OFFICE
CERTIFICATE OF CORRECTION

PATENT NO. : 4,941,503

DATED : JULY 17, 1990

INVENTOR(S) : HENRY H. HUBNER

It is certified that error appears in the above-identified patent and that said Letters Patent is hereby corrected as shown below:

Column 4, line 17, "surface portion 79", should read -- surface portion 74 --.

Signed and Sealed this

Thirty-first Day of December, 1991

Attest:

HARRY F. MANBECK, JR.

*Attesting Officer*  *Commissioner of Patents and Trademarks*